US009851337B2

(12) United States Patent
Lee et al.

(10) Patent No.: US 9,851,337 B2
(45) Date of Patent: Dec. 26, 2017

(54) UNIVERSAL WATER CONDITION MONITORING DEVICE

(71) Applicants: Kye-Shin Lee, Copley, OH (US); Ajay Mahajan, North Canton, OH (US)

(72) Inventors: Kye-Shin Lee, Copley, OH (US); Ajay Mahajan, North Canton, OH (US)

(73) Assignee: The University of Akron, Akron, OH (US)

( * ) Notice: Subject to any disclaimer, the term of this patent is extended or adjusted under 35 U.S.C. 154(b) by 177 days.

(21) Appl. No.: 14/563,130

(22) Filed: Dec. 8, 2014

(65) Prior Publication Data
US 2015/0160178 A1    Jun. 11, 2015

Related U.S. Application Data

(60) Provisional application No. 61/912,604, filed on Dec. 6, 2013.

(51) Int. Cl.
*G01N 33/18* (2006.01)
*G01N 27/30* (2006.01)
*G01N 27/02* (2006.01)
*G01K 13/00* (2006.01)
*G01K 7/16* (2006.01)

(52) U.S. Cl.
CPC .......... *G01N 33/1886* (2013.01); *G01K 7/16* (2013.01); *G01K 13/00* (2013.01); *G01N 27/02* (2013.01); *G01N 27/302* (2013.01); *G01N 33/1853* (2013.01)

(58) Field of Classification Search
CPC .......... G01N 33/1853; G01N 33/1886; G01N 27/302; G01N 27/02; G01N 27/30; G01N 27/27; G01K 7/16; G01K 13/00
See application file for complete search history.

(56) References Cited

U.S. PATENT DOCUMENTS 3,258,682 A * 6/1966 Maurer ............ G01N 27/4167
                                               204/408
3,298,944 A * 1/1967 Luck .................. G01N 27/4166
                                               204/271

(Continued)

FOREIGN PATENT DOCUMENTS

DE       4121397 A1 * 1/1993  ......... G01N 33/1886
JP    2010060376 A  *  3/2010

OTHER PUBLICATIONS

Machine translation of JP 2010060376 A.*

*Primary Examiner* — David Bolduc
(74) *Attorney, Agent, or Firm* — Renner Kenner Greive Bobak Taylor & Weber

(57) ABSTRACT

The present invention is directed to a water condition monitoring device and related methods of use that significantly reduce the cost of the water condition monitoring devices by replacing the expensive and bulky multiple sensor electrodes of currently available devices with a single set of two or three metal electrodes to detect and/or measure such water quality parameters as pH, electric conductivity, temperature, and dissolved oxygen content. A microcontroller activates each sensor one at a time in a continuous loop, processing the sensor signals into near real time water condition data, which may be stored, displayed, or sent to a remote location for storage or display.

17 Claims, 5 Drawing Sheets

(56) References Cited

U.S. PATENT DOCUMENTS

| | | | | |
|---|---|---|---|---|
| 3,926,747 A * | 12/1975 | Newby | C25D 3/48 | 204/DIG. 7 |
| 3,956,094 A * | 5/1976 | Capuano | G01N 27/4168 | 204/284 |
| 4,157,657 A * | 6/1979 | Hinchman | G01N 33/1886 | 254/333 |
| 4,338,175 A * | 7/1982 | Binder | G01N 27/4035 | 204/421 |
| 4,506,226 A * | 3/1985 | Luce | G01N 27/27 | 204/406 |
| 4,763,537 A * | 8/1988 | Scott | G01N 33/1886 | 396/26 |
| 4,764,271 A * | 8/1988 | Acosta | C02F 1/02 | 210/143 |
| 4,777,444 A * | 10/1988 | Beijk | G01N 27/4165 | 204/401 |
| 4,912,417 A * | 3/1990 | Gibboney | G01N 27/4165 | 204/400 |
| 4,940,946 A * | 7/1990 | Nazaryan | G01N 33/1886 | 324/149 |
| 4,998,068 A * | 3/1991 | McKee, Jr. | G01N 27/4166 | 324/438 |
| 5,103,179 A * | 4/1992 | Thomas | G01N 33/1886 | 204/412 |
| 5,108,578 A * | 4/1992 | Somes | G01N 27/4165 | 204/400 |
| 5,126,937 A * | 6/1992 | Yamaguchi | A61B 5/145 | 374/173 |
| 5,218,304 A * | 6/1993 | Kinlen | G01N 27/4166 | 204/412 |
| 5,342,510 A * | 8/1994 | Eden | B01J 19/0006 | 204/433 |
| 5,483,164 A * | 1/1996 | Moss | G01N 33/1886 | 204/406 |
| 5,543,717 A * | 8/1996 | Kordas | G01R 27/22 | 324/439 |
| 5,581,189 A * | 12/1996 | Brenn | G01N 33/18 | 204/402 |
| 5,798,940 A * | 8/1998 | Bratton | G01V 9/007 | 204/406 |
| 5,804,971 A * | 9/1998 | Cumming | G01N 27/286 | 204/406 |
| 5,945,830 A * | 8/1999 | Magowan | G01N 27/283 | 204/433 |
| 5,986,261 A * | 11/1999 | Lewis | B82Y 35/00 | 136/228 |
| 6,021,664 A * | 2/2000 | Granato | E21B 49/084 | 166/264 |
| 6,119,508 A * | 9/2000 | Tarui | G01N 27/4166 | 324/438 |
| 6,183,695 B1 * | 2/2001 | Godec | G01N 27/06 | 422/76 |
| 6,732,568 B2 * | 5/2004 | Dimarzo | G01N 25/18 | 73/25.01 |
| 7,189,314 B1 * | 3/2007 | Pace | G01N 33/1886 | 204/412 |
| 7,465,358 B2 * | 12/2008 | Weidman | C23C 18/1601 | 118/429 |
| 2002/0135377 A1 * | 9/2002 | Farruggia | G01N 33/18 | 324/441 |
| 2002/0167322 A1 * | 11/2002 | He | G01R 27/22 | 324/441 |
| 2003/0112012 A1 * | 6/2003 | Mosley | G01N 27/4167 | 324/446 |
| 2003/0143752 A1 * | 7/2003 | Feldsine | G01N 21/76 | 436/164 |
| 2003/0180186 A1 * | 9/2003 | Carson | G01N 33/1853 | 422/82.02 |
| 2005/0009192 A1 * | 1/2005 | Page | C02F 1/006 | 436/55 |
| 2005/0207939 A1 * | 9/2005 | Roussi | G01N 33/1886 | 422/68.1 |
| 2007/0084722 A1 * | 4/2007 | Sagawa | G01N 27/4168 | 204/403.01 |
| 2007/0214872 A1 * | 9/2007 | Ammann | G01N 27/4165 | 73/53.01 |
| 2008/0011061 A1 * | 1/2008 | Sihalla | G01N 1/14 | 73/64.56 |
| 2009/0123340 A1 * | 5/2009 | Knudsen | G01N 33/1886 | 422/105 |
| 2009/0149421 A1 * | 6/2009 | Buschmann | A61K 8/19 | 514/55 |
| 2010/0285210 A1 * | 11/2010 | Choi | G01K 13/00 | 427/125 |
| 2011/0278168 A1 * | 11/2011 | Zhuiykov | G01N 33/18 | 204/407 |
| 2011/0297539 A1 * | 12/2011 | Sagawa | G01N 27/4168 | 204/400 |
| 2012/0091008 A1 * | 4/2012 | Muir | G01N 27/333 | 205/316 |
| 2012/0145561 A1 * | 6/2012 | Coulon | G01N 33/1886 | 205/778.5 |
| 2012/0216605 A1 * | 8/2012 | Silveri | G01N 27/4168 | 73/61.41 |
| 2012/0234696 A1 * | 9/2012 | Mosley | G01N 27/301 | 205/775 |
| 2014/0374251 A1 * | 12/2014 | Soccol | G01N 27/302 | 204/415 |

* cited by examiner

UNIVERSAL WATER CONDITION MONITORING DEVICE

CROSS REFERENCE TO RELATED APPLICATIONS

This application claims the benefit of U.S. provisional patent application Ser. No. 61/912,604 entitled "Universal Water Condition Monitoring Device," filed Dec. 6, 2014, and incorporated herein by reference in its entirety.

REFERENCE TO GOVERNMENT SUPPORT

The invention was developed at least in part with the support of United States National Science Foundation grant number NSF1000002370 and Ohio Third Frontier TVSF Grant (phase-I) grant number 1000002210ODOD. The government may have certain rights in the invention.

FIELD OF THE INVENTION

One or more embodiments of the present invention relates to a device for monitoring water conditions. In certain embodiments, the present invention relates to a device and related method for monitoring pH, temperature, electrical conductivity, and dissolved oxygen content of water using a single set of electrodes.

BACKGROUND OF THE INVENTION

Recently, there is an increased demand for user friendly and smart water condition monitoring devices for detecting and/or measuring water parameters such as pH, electric conductivity (EC), temperature, and dissolved oxygen content for a variety of applications including hydroponic plant growing, aquariums, swimming pools and spas. The majority of existing water condition monitoring devices are manually operated, hard to use for beginners, and only measure a single condition (only pH or EC), yet are costly with prices ranging from $50 to more than $500. Moreover, in order to measure multiple water quality parameters using existing technologies, bulky multiple sensor electrodes are used to detect each condition to be tested, making the overall monitoring system both costly and cumbersome to use.

What is needed in the art are easy, user friendly, and smart water condition monitoring devices that do not require bulky multiple sensor electrodes and are also economical.

SUMMARY OF THE INVENTION

One or more embodiments of the present invention provides a novel wireless water condition monitoring device that solves some of the problems found in the existing wireless water condition monitoring devices mentioned above. The approach used in one or more or more embodiments of the present invention significantly reduces the cost of these water condition monitoring devices by eliminating the bulky multiple sensor electrodes, which are a significant drawbacks of existing water condition monitoring devices. These user friendly and smart wireless water condition monitoring devices reduce cost by using only one set of two (or sometimes three) metal sensing electrodes to detect such water quality parameters as pH, electric conductivity (EC), temperature, and dissolved oxygen content. The wireless water condition monitoring device of embodiments of the present invention is low cost, compact, requires only one electrode pair, and easy to use.

In a first aspect, one or more embodiments of the present invention are directed to a water condition monitoring device comprising: a first electrode and a second electrode, wherein said first and second electrodes are made from different conductive metals; a pH sensing unit coupled to said first and second electrodes; an electrical conductivity sensing unit coupled to said first and second electrodes; and a microcontroller, coupled to said pH sensing unit and said electrical conductivity sensing unit. In one or more embodiments, the water condition monitoring device also comprises a temperature sensing unit coupled to said first or said second electrode and said microcontroller. In one or more embodiments, the water condition monitoring device may include any one or more of the above referenced embodiments of the first aspect of the present invention further comprising a dissolved oxygen sensing unit coupled to said first and second electrodes, a third electrode, and said microcontroller.

In one or more embodiments, the water condition monitoring device may include any one or more of the above referenced embodiments of the first aspect of the present invention wherein said first electrode further comprises a metal selected from the group consisting of copper, zinc, nickel, platinum, silver, gold, and combinations thereof. In one or more embodiments, the water condition monitoring device may include any one or more of the above referenced embodiments of the first aspect of the present invention wherein said second electrode further comprises a metal selected from the group consisting of copper, zinc, nickel, platinum, silver, gold, and combinations thereof.

In one or more embodiments, the water condition monitoring device may include any one or more of the above referenced embodiments of the first aspect of the present invention further comprising a display coupled to said microcontroller. In one or more embodiments, the water condition monitoring device may include any one or more of the above referenced embodiments of the first aspect of the present invention further comprising an interface for storage or display of measured pH, electrical conductivity, temperature and/or dissolved oxygen values at a remote location.

In a second aspect, one or more embodiments of the present invention are directed to a method of monitoring water conditions using a single set of metal electrodes comprising: placing a first metal electrode and a second metal electrode in a quantity of water to be monitored, wherein said first and second metal electrodes are coupled to a plurality of sensors, each sensor measuring an attribute of the water to be monitored; and sequentially activating each one of said plurality of sensors to measure each attribute of the water to be monitored and generating a corresponding output voltage.

In one or more embodiments, said plurality of sensors are coupled to a microcontroller, said method further comprising: sending the output voltage produced by each one of the plurality of sensors to the microcontroller; and comparing the output voltage of each sensor to a corresponding table of known attribute values to find an attribute value that corresponds to the output voltage. In one or more embodiments, method of monitoring water conditions may include any one or more of the above referenced embodiments of the second aspect of the present invention further comprising storing or displaying the attribute value that corresponds to the output voltage of the sensor. In one or more embodiments, method of monitoring water conditions may include any one or more of the above referenced embodiments of the second aspect of the present invention wherein said first metal electrode and said second metal electrodes are made from different conductive metals.

In one or more embodiments, method of monitoring water conditions may include any one or more of the above referenced embodiments of the second aspect of the present invention wherein the plurality of sensors comprises a pH sensor for measuring the pH of the water and an electrical conductivity sensor for measuring the electrical conductivity of the water, said method further comprising: sending a signal activating said pH sensor and causing it to measure the voltage difference between said first metal electrode and said second metal electrode and generate a first output voltage corresponding to the pH of the water; transmitting the first output voltage to a microcontroller; converting the first output voltage to a corresponding pH value in said microcontroller; storing or displaying said corresponding pH value; sending a signal deactivating said pH sensor; sending a signal activating said electrical conductivity sensor and causing it to apply an AC voltage across said first and second metal electrodes thereby generating a second output voltage that is proportional to the electrical conductivity of the water; transmitting said second output voltage to said microcontroller; converting said second output voltage to a corresponding electrical conductivity value in said microcontroller; storing or displaying said electrical conductivity value; and sending a signal deactivating said electrical conductivity sensing unit.

In one or more embodiments, method of monitoring water conditions may include any one or more of the above referenced embodiments of the second aspect of the present invention wherein the plurality of sensors for measuring an attribute of the water to be monitored further comprise a temperature sensor for measuring the temperature of the water, said temperature sensor coupled to one of said first and second metal electrodes, said method further comprising: sending a signal activating said temperature sensor and causing it to apply a voltage to one of said first or said second metal electrodes and to measure the resistance; converting the resistance to a corresponding output voltage and sending said output voltage to the microcontroller; converting said output voltage to a corresponding temperature value in said microcontroller; storing or displaying said temperature value; and sending a signal deactivating said temperature sensor.

In one or more embodiments, method of monitoring water conditions may include any one or more of the above referenced embodiments of the second aspect of the present invention wherein the plurality of sensors for measuring an attribute of the water to be monitored further comprise a dissolved oxygen sensing unit for measuring the level of dissolved oxygen in the water, the method further comprising: sending a signal activating said dissolved oxygen sensing unit and causing it to apply an oxidation potential voltage across said first and second metal electrodes thereby generating causing the dissolved oxygen in the water to come out of solution; measuring the voltage difference between the first metal electrode or said second metal electrode and a third metal electrode and generating a corresponding output voltage; transmitting said output voltage to the microcontroller; converting said output voltage to a dissolved oxygen value in said microcontroller; storing or displaying said dissolved oxygen value; and sending a signal deactivating said dissolved oxygen sensing unit.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

In general, the present invention is directed to a water condition monitoring device and related methods of use that significantly reduces the cost of the water condition monitoring device. Such cost reduction is achieved by replacing the expensive and bulky multiple sensor electrodes of currently available water condition monitoring devices with a single set of metal electrodes to detect such water quality parameters as pH, electric conductivity (EC), temperature, and dissolved oxygen content in applications including such things as hydroponic plant growing, aquariums, swimming pools and spas. While the liquid to be tested by the water condition monitoring devices and/or methods described herein is generally referred to as "water," the present invention is not to be so limited and includes any electrolytic solutions, mixtures, suspensions, containing water ($H_2O$).

As used herein, the term "water quality parameter(s)" or more broadly "parameter(s)" refers to a measurable attribute of the water or other electrolyte being tested including, including, but not limited to, its pH, electric conductivity (EC), temperature, and dissolved oxygen content. The term a parameter value refers to a measured value for a parameter being tested expressed as is conventional for the attribute being tested, such as a pH or a temperature in degrees centigrade.

Figure 1:
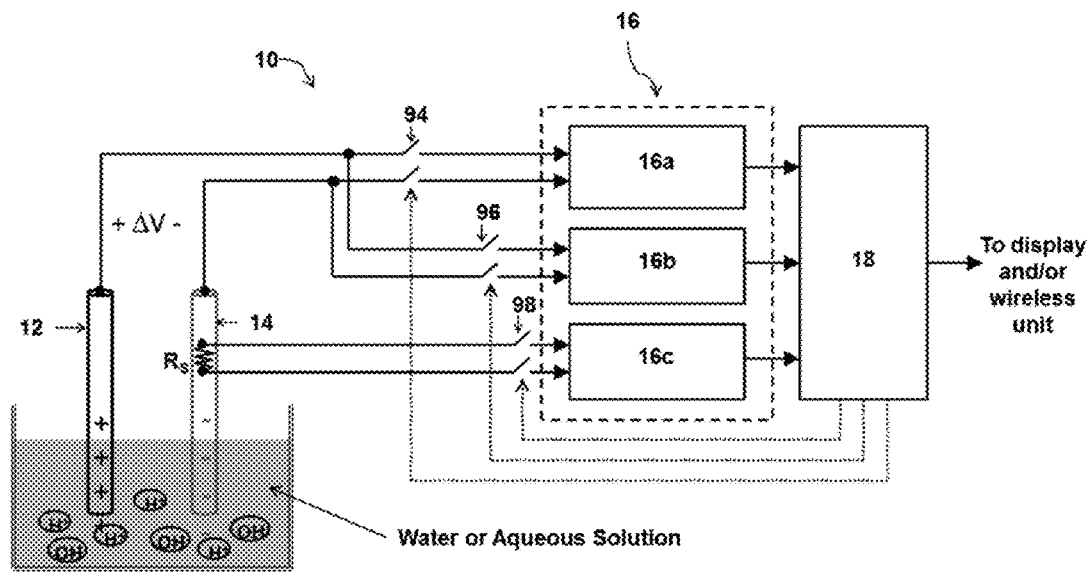
FIG. 1 is a block diagram showing the operation of a water condition monitoring device according to at least one embodiment of the present invention.

Referring now to FIG. 1, a water condition monitoring device according to one or more embodiments of the present invention is shown, generally indicated by the numeral 10. Water condition monitoring device 10 includes a first metal electrode 12 and a second metal electrode 14. The first and second metal electrodes 12, 14 may be made of any conductive metal or metal alloy including, but not limited to copper, zinc, nickel, platinum, silver, gold and combinations and/or alloys thereof. In some embodiments, the first metal electrode 12 and the second metal electrode 14 may be made from different conductive metals or metal alloys. In some embodiments, one of the first metal electrode 12 and the second metal electrode 14 may be made from and/or substantially comprise zinc and the other of the first metal electrode 12 and the second metal electrode 14 may be made from and/or substantially comprise copper.

Connected in parallel to one or both of the first metal electrode 12 and the second metal electrode 14 are two or more sensors 16. Sensors 16 measure and/or detect water condition parameters and are not particularly limited except that they must be able to detect and/or measure a desired parameter based upon input received from the metal electrodes 12, 14. Water condition parameters that may be detected and/or measured by embodiments of the present invention include, without limitation, pH, electric conductivity (EC), temperature, and dissolved oxygen content. When activated, each one of sensors 16 generates an output that is sent to a microcontroller 18 coupled thereto for further signal processing, whereupon the processed data can be displayed on a display unit in communication with the microcontroller 18. In some embodiments, the data may be transferred to another data storage unit or display unit through a wireless link in communication with the microcontroller 18.

In the embodiment shown in FIG. 1, a pH sensor circuit 16a, electrical conductivity (EC) sensor circuit 16b, and temperature sensor circuit 16c are each attached to one or both of the first metal electrode 12 and the second metal electrode 14 and to a microcontroller 18. A pH sensor circuit 16a may be any suitable pH sensor circuit known in the art that is capable of working with a single set of conductive metal electrodes.

In some embodiments, pH sensor circuits according to one or more embodiments of the present invention detect the pH in the water or other electrolyte being tested by passively detecting the voltage difference between the first and second electrodes 12, 14 generated by the H$^+$ and OH$^-$ ions in the water or other electrolyte being tested. It is important in these embodiments that the first and second electrodes 12, 14 are made up of different metals (e.g. copper and zinc) Since electrodes 12, 14 are made from different metals, one of the electrodes (for example the first electrode 12) will have more positive atoms and the other electrode (second electrode 14) will contain more negative atoms. And as will be appreciated by those of skill in the art, the reduction process will dominate the more positive electrode 12 and oxidation will mainly occur in the more negative electrode 14. As a result, positive ions will be released from second electrode 14, which will make the first electrode 12 positively charged and second electrode 14 negatively charged. Thus, there will be a positive voltage difference ($\Delta V$) between the two electrodes 12, 14. The pH measurement will be based on the value of $\Delta V$.

As set forth above, a passive DC measurement approach has been used to measure H$^+$ concentration ([H$^+$]) or pH (pH=−log(H$^+$)) and two different metal electrodes will produce a voltage difference that is proportional to [H$^+$] concentration of the water or other electrolyte being tested. It should be understood that for a pH less than 7.0, there will be more H$^+$ ions in the solution which will obstruct the positive ions being released from the second electrode 14, making it less negative compared to the first electrode 12. On the other hand, if the pH is higher than 7.0, OH$^-$ ions will be dominant, and this will help the positive ions being released from the second electrode 14, which will make it relatively more negative than the first electrode 12. Accordingly, the $\Delta V$ will increase as the pH increases, and vice versa. The pH sensor circuit 16a will generate an output voltage that corresponds to the pH of the solution based upon the $\Delta V$. The output voltage is then sent to the microcontroller 18 for processing as previously discussed.

Figure 2:
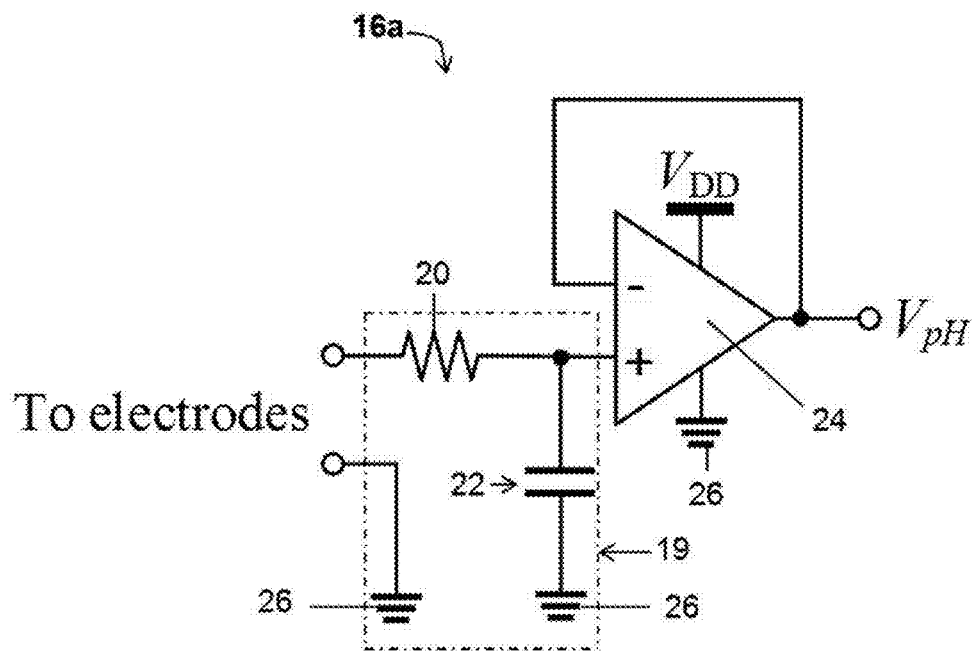
FIG. 2 is a schematic circuit diagram showing the operation of a pH sensor for a water condition monitoring device according to at least one embodiment of the present invention.

In some embodiments, the pH sensor circuit 16a may comprise resister 20, capacitor 22, operational amplifier 24, grounds 26 and supply voltage ($V_{DD}$) arranged as shown in FIG. 2, to produce output voltage $V_{pH}$. The resister 20 may be any suitable resister such as a fixed carbon resister, wire wand resister, metal film resistor, or the like. One or ordinary skill in the art will be able to select a suitable resistor without undue experimentation. In some embodiments, resister 20 may have a resistance of about 33 k$\Omega$. Capacitor 22 may be any suitable capacitor such as a thin film capacitor, electrolytic capacitor, ceramic capacitor, or the like. One or ordinary skill in the art will be able to select a suitable capacitor without undue experimentation. In some embodiments, resister 20 may be a 33 k$\Omega$ resister and capacitor 22 may be a 0.01 $\mu$F capacitor. Operational amplifier 24 may be any suitable operational amplifier known in the art. One or ordinary skill in the art will be able to select a suitable operational amplifier without undue experimentation. In some embodiments, operational amplifier 24 may be an OP 741 operational amplifier commercially available through Texas Instruments Inc. (Dallas, Tex.). In some embodiments, the supply voltage ($V_{DD}$) may be a DC power source of from about 3.3V to about 5V depending upon the output range, but may be any appropriate value necessary to operate the operational amplifier 24. In these embodiments, the output ($V_{pH}$) by pH sensor circuit 16a is then sent to microcontroller 18 as an output voltage for further processing as described above.

Since in some embodiments, the water condition monitoring device 10 of the present invention uses the same set of electrodes (electrodes 12, 14) to measure both pH and electrical conductivity (EC), and it is necessary to eliminate the interference between the EC sensor circuit 16b (described below) that works with 3.21 kHz and the pH sensor circuit 16a that operates with direct current (DC). As a result, in some embodiments, a passive low-pass filter 19, comprised of resistor 20 ($R_1$), capacitor 22 ($C_1$), and ground 26, is added to the input stage of the pH circuit. The cut-off frequency $f_{cut-off}$ is given as:

$$f_{cut-off} = \frac{1}{2\pi R_1 C_1} \quad (3)$$

By setting resister 20 to 33 k$\Omega$ and capacitor 22 to 0.01 $\mu$F, for example, the $f_{cut-off}$ is less than 500 Hz. This will eliminate the interference from the EC circuit. In addition, in some embodiments, a single-supply voltage buffer may be added between the electrode and microcontroller 18 to isolate the sensor electrode and microcontroller 18.

Turning again to FIG. 1, electric conductivity (EC) sensor circuit 16b may be any suitable EC sensor circuit known in the art that is capable of working with a single set of conductive metal electrodes. In some embodiments, the EC sensor circuit 16b may measure the electrical conductivity of the water or other electrolyte being tested by applying an AC voltage across the two electrodes 12, 14, thereby generating an output voltage that is proportional to the conductivity of the solution. In some embodiments, the AC voltage applied across the electrodes 12 and 14 may have a frequency of from about 1 kHz to about 20 kHz. In some embodiments, the AC voltage applied across the electrodes 12 and 14 may have a frequency that is from about 1 kHz to about 10 kHz. In some embodiments, the AC voltage applied across the electrodes 12 and 14 may have a frequency that is from about 1 kHz to about 5 kHz. In some embodiments, the AC voltage applied across electrodes 12 and 14 may have a frequency of approximately 1 kHz. In some embodiments, the AC voltage applied across electrodes 12 and 14 may have a frequency of approximately 3.21 kHz. In one or more embodiments of the present invention, the EC sensor circuit 16b generates a DC output voltage, which is then sent to microcontroller 18 for further processing as described above.

Figure 3:
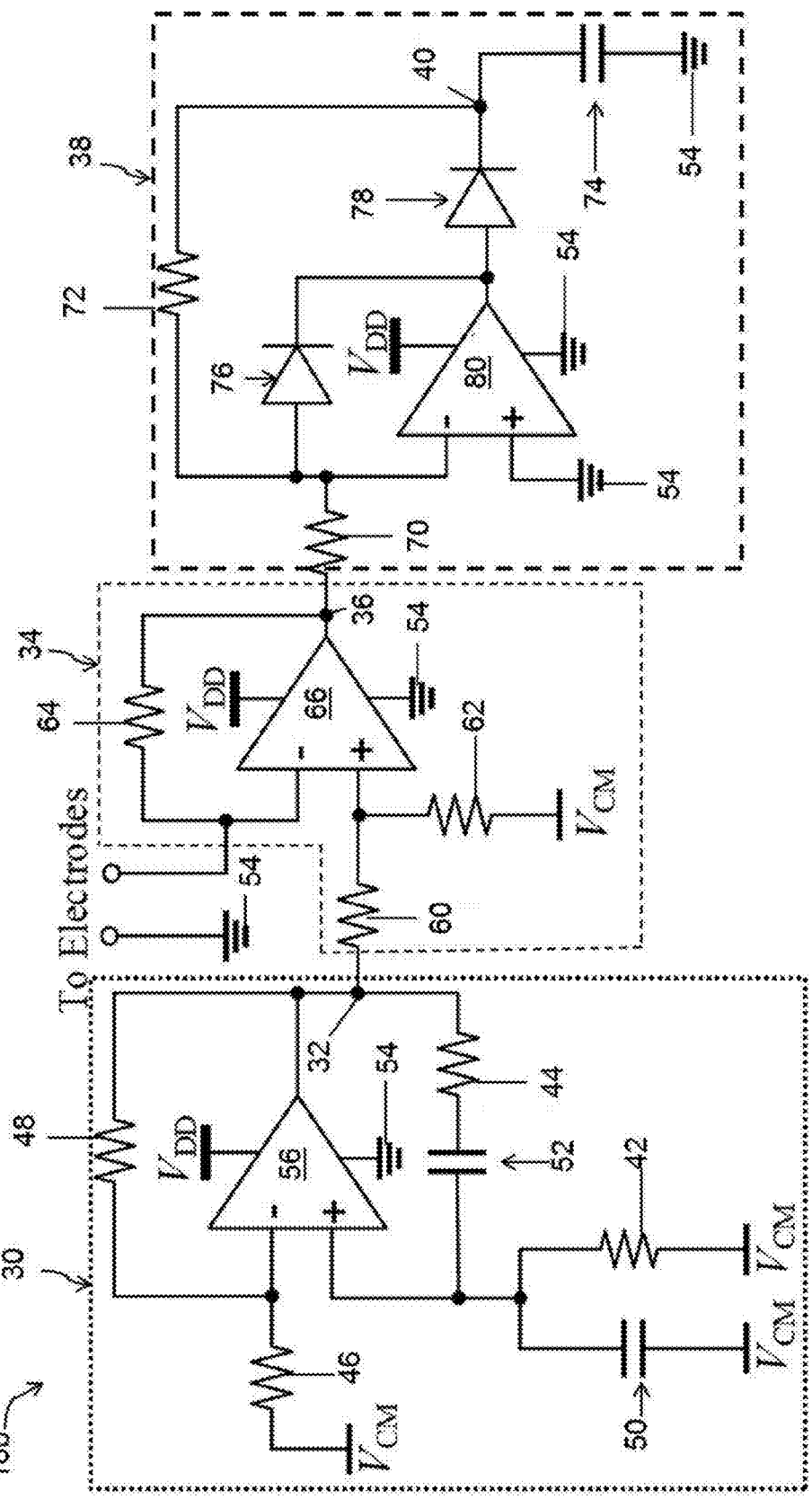
FIG. 3 is a schematic circuit diagram showing the operation of an electrical conductivity sensor for a water condition monitoring device according to at least one embodiment of the present invention.

In some embodiments, the EC sensor circuit 16b may have the general layout shown in FIG. 3. The EC sensor circuit 16b of the embodiments shown in FIG. 3 comprises three stages/circuits: an oscillator stage/circuit 30 which produces a sinusoidal AC voltage ($V_{out1}$) at node 32; a detection stage/circuit 34 coupled to node 32, which utilizes $V_{out1}$ to detect the electrical conductivity of the water or other electrolyte being tested and produces an AC voltage ($V_{out2}$) at node 36; and an AC to DC conversion stage/circuit 38 coupled to node 36, which produces a DC voltage ($V_{out3}$) at node 40 corresponding to the conductivity of the water sample being tested. The DC output voltage ($V_{out3}$) is then sent to microcontroller 18 for further processing as described above.

As can be seen in the embodiments of FIG. 3, oscillator phase/circuit 30 may comprise supply power source ($V_{DD}$), common mode voltage sources ($V_{CM}$), first resister 42 ($R_1$), second resister 44 ($R_2$), third resister 46 ($R_3$), fourth resister 48 ($R_4$), first capacitor 50 ($C_1$), second capacitor 52 ($C_2$), grounds 54 and first operational amplifier 56 arranged as shown in FIG. 3, to produce a first output voltage MO at node 32. In the embodiment of FIG. 3, the oscillation stage 30 uses a conventional Wien-bridge oscillator to generate a sinusoidal waveform. In particular, the Wien-bridge oscillator provides negative feedback to produce a stable wave form. It should be appreciated, however, that the present invention is not to be so limited and any conventional oscillator circuit that produces a suitable stable wave form may be used.

$V_{DD}$ may be a DC power source of from about 3.3V to about 5V depending upon the output range, but may be any appropriate value necessary to operate the first operational amplifier 56. In some embodiments, $V_{CM}$ may be from about 1.65V to about 2.5V, depending upon the value of $V_{DD}$. In some embodiments, $V_{CM}$ is about 1.65V. First resister 42 ($R_1$), second resister 44 ($R_2$), third resister 46 ($R_3$), fourth resister 48 ($R_4$) may be any suitable resister such as a fixed carbon resister, wire wand resister, metal film resister, or the like. One or ordinary skill in the art will be able to select a suitable resisters for first resister 42 ($R_1$), second resister 44 ($R_2$), third resister 46 ($R_3$), fourth resister 48 ($R_4$) without undue experimentation. In some embodiments, first resister 42 and second resister 44 may have a resistance of about 3.3 kΩ. In some embodiments, third resister 46 may have a resistance of about 22 kΩ. In some embodiments, fourth resister 48 may have a resistance of about 43 kΩ. In some embodiments, fourth resister 48 ($R_4$) may be a variable resister.

First capacitor 50 and second capacitor 52 may be any suitable capacitor such as a thin film capacitor, electrolytic capacitor, ceramic capacitor, or the like. One or ordinary skill in the art will be able to select a suitable capacitor without undue experimentation. In some embodiments, first capacitor 50 ($C_1$) may have a capacitance of about 0.1 μF. In some embodiments, second capacitor 52 ($C_2$) may have a capacitance of about 0.1 μF. First operational amplifier 56 may be any suitable operational amplifier known in the art. One or ordinary skill in the art will be able to select a suitable operational amplifier without undue experimentation. In some embodiments, the operational amplifier 56 may be an OP741 operational amplifier commercially available from Texas Instruments Inc. (Dallas, Tex.). As set forth above, in the oscillator circuit 30 of FIG. 3, the output voltage $V_{out1}$ will be a sinusoidal AC voltage.

In embodiments shown in FIG. 3, the oscillator circuit 30 may be implemented using a single-supply rail-to-rail operational amplifier, such as OPA337 (Texas Instrument Inc.), and passive components, 42 ($R_1$), 44 ($R_2$), 50 ($C_1$), and 52 ($C_2$), to make the oscillation frequency:

$$f_{oc} = \frac{1}{2\pi}\sqrt{\frac{1}{R_1 C_1 R_2 C_2}} \quad (1)$$

It should be noted that neither 42 ($R_1$) and 44 ($R_2$), nor 50 ($C_1$) and 52 ($C_2$) are necessarily required to be equal. Generally, for measuring the conductivity of electrolytes, a frequency of from between about 1 kHz and 20 kHz may be used. In some embodiments, a frequency of from between about 1 kHz and 5 kHz may be used. In some embodiments, a frequency of from between about 2 kHz and 4 kHz may be used. In some applications, a frequency of about 1 kHz may be used. For some embodiments of the present invention used with hydroponic applications, however, the optimum frequency may be set to about 3.21 kHz. For the circuit shown in FIG. 3, $R_1$ 42 and $R_2$ 44 may be set to about 3.3 kΩ, $C_1$ 50 and $C_2$ 52 may be set to about 15 nF and $R_4=R_3/2=22$ kΩ but as those of skill in the art will recognize, these values will depend upon the output range of the operational amplifier. However, in some embodiments of the present invention, the oscillator circuit shown in FIG. 3 has been found to generate a stable oscillation with the resistor and capacitor values set forth above.

The EC sensor circuit 16b shown in FIG. 3 further comprises a detection stage/circuit 34, which uses the AC output voltage signal ($V_{out1}$) from oscillator phase/circuit 30 to detect the electrical conductivity of the electrolyte (water) being tested and produces a corresponding AC voltage signal ($V_{out2}$) at node 36. In these embodiments, the detection stage 34 may comprise a supply power source ($V_{DD}$), common mode voltage sources ($V_{CM}$), a fifth resister 60 ($R_5$), sixth resister 62 ($R_6$), seventh resister 64 ($R_7$), grounds 54, and a second operational amplifier 66 arranged as shown in FIG. 3 to produce a second output voltage ($V_{out2}$) at node 36.

In some embodiments, $V_{DD}$ may be a DC power source of from about 3.3V to about 5V depending upon the output range of the operational amplifier, but may be any appropriate value necessary to operate the second operational amplifier 66. In some embodiments, $V_{DD}$ may be a 9V DC power source supplied by a conventional 9V battery. In some embodiments, $V_{CM}$ is from 1.65V to 2.5V, depending upon the value of $V_{DD}$. In some embodiments, $V_{CM}$ is 1.65V. Fifth resister 60 ($R_5$), sixth resister 62 ($R_6$), and seventh resister 64 ($R_7$) may be any suitable resister such as a fixed carbon resister, wire wand resister, metal film resister, or the like. One or ordinary skill in the art will be able to select a suitable resisters for fifth resister 60 ($R_5$), sixth resister 62 ($R_6$), and seventh resister 64 ($R_7$) without undue experimentation. In some embodiments, fifth resister 60 ($R_5$) may have a resistance of about 100 kΩ. In some embodiments, fifth resister 60 ($R_5$) may be a variable resister. In some embodiments, sixth resister 62 ($R_6$) may have a resistance of about 1 kΩ. In some embodiments, seventh resister 64 ($R_7$) may have a resistance of about 2 kΩ. Second operational amplifier 66 may be any suitable operational amplifier known in the art. One or ordinary skill in the art will be able to select a suitable capacitor without undue experimentation. In some embodiments, second operational amplifier 66 may be an OP741 operational amplifier commercially available through Texas Instruments Inc. (Dallas, Tex.).

In some embodiments, a variable resistor may be used for $R_4$ 48 and $R_5$ 60 of EC sensor circuit 16b (See FIG. 3) to tune the oscillation frequency and to adjust the amplitude of the AC voltage that is applied between the sensor electrodes 12, 14. In this way, it is believed that the dynamic range and resolution of the EC circuit may be adjusted depending on the application conditions.

As can be seen in FIG. 3, the second operational amplifier 66 is applying the sine wave voltage ($V_{out1}$) between the two electrodes 12, 14 with attenuating voltage divider 48 ($R_4$) and 60 ($R_5$). As the conductivity of the electrolyte (water) changes, the equivalent resistance between the first and second electrodes 12, 14 changes, and as a result, changes the peak-to-peak voltage of the second stage output ($V_{out2}$), which is given as:

$$V_{out2} = \left(1 + \frac{R_7}{R_E}\right)\left(\frac{R_6}{R_5 + R_6}\right)V_{out1} \quad (2)$$

where $R_E$ is inversely proportional to the conductivity of the water or other electrolyte being tested.

The EC sensor circuit 16b shown in FIG. 3 further comprises an AC to DC conversion stage/circuit 38 that receives the AC output signal ($V_{out2}$), of the detection stage 34 and converts it to a DC voltage output signal ($V_{out3}$) that corresponds to the conductivity of the water sample being tested. As shown in FIG. 3, the AC to DC conversion stage/circuit 38 may comprise a supply power source ($V_{DD}$) common mode voltage sources ($V_{CM}$), an eighth resister 70 ($R_8$), ninth resister 72 ($R_9$), a load capacitor 74 ($C_L$), grounds 54, a first diode 76 ($D_1$), second diode 78 ($D_2$), and a third operational amplifier 80, arranged as shown in FIG. 3, to produce a third output voltage ($V_{out3}$) at node 40. In these embodiments, DC voltage output signal ($V_{out3}$) by EC sensor circuit 16b is then sent to microcontroller 18 as an output voltage for further processing as described above.

In some embodiments, $V_{DD}$ may be a DC power source of from about 3.3V to about 5V depending upon the output range, but may be any appropriate value necessary to operate the third operational amplifier 80. In some embodiments, $V_{DD}$ may be a 9V DC power source supplied by a conventional 9V battery. Eighth resister 70 ($R_8$) and ninth resister 72 ($R_9$) may be any suitable resister such as a fixed carbon resister, wire wand resister, metal film resister, or the like. One or ordinary skill in the art will be able to select a suitable resistors for eighth resister 70 ($R_8$) and ninth resister 72 ($R_9$) without undue experimentation. In some embodiments, eighth resister 70 ($R_8$) may have a resistance of about 8.2 kΩ. In some embodiments, ninth resister 74 ($R_9$) may have a resistance of about 8.2 kΩ.

Load capacitor 74 ($C_L$), may be any suitable capacitor such as a thin film capacitor, electrolytic capacitor, ceramic capacitor, or the like. One or ordinary skill in the art will be able to select a suitable load capacitor without undue experimentation. Third operational amplifier 80 may be any suitable operational amplifier known in the art. One or ordinary skill in the art will be able to select a suitable operational amplifier without undue experimentation. In some embodiments, the third operational amplifier 80 may be a Texas Instruments OP741 operational amplifier.

First diode 76 ($D_1$) and second diode 78 ($D_2$) may be any suitable diode. One or ordinary skill in the art will be able to select suitable diodes for first diode 76 ($D_1$) and second diode 78 ($D_2$) without undue experimentation. In some embodiments, first diode 76 ($D_1$) may be a High Conductance Fast Diode (Part No. 1N4148) made by Fairchild Semiconductors (San Jose, Calif.). In some embodiments, second diode 78 ($D_2$) may High Conductance Fast Diode (Part No. 1N4148) made by Fairchild Semiconductors (San Jose, Calif.).

In these embodiments, when input voltage $V_{out2}$ is below $V_{CM}$ (1.65 V), $D_1$ 76 is off and $D_2$ 78 is on. So, the output voltage $V_{out3}$ tracks the input voltage ($V_{out2}$) with a gain of ($-R_9/R_8$). When the input is greater than $V_{CM}$, $D_1$ 76 is on and $D_2$ 78 is off so that $D_2$ 78 becomes an open circuit and the output becomes $V_{CM}$ since the other terminal of $R_9$ 72 is connected to the virtual ground of the third operational amplifier 80. Using the capacitor 74 ($C_L$) as a load, the circuit can detect the peak voltage of $V_{out2}$, and generate a DC voltage that is equal to the peak voltage. This DC voltage ($V_{out3}$) corresponds to the conductivity of the water or other electrolyte being tested and is provided as an output voltage to microcontroller 18.

Turning again to FIG. 1, temperature sensor circuit 16c may be any suitable temperature sensor known in the art that is capable of working with a conductive metal electrode and may include, without limitation, a Low Voltage Temperature Sensor (part no. TMP35) commercially available through Analog Device (Norwood, Mass.). In some embodiments, the temperature sensor circuit 16c may detect the temperature by measuring the resistance variation of one of electrodes 12 and 14 over a known length of electrode l. (See FIGS. 1, 4). The temperature sensor will convert the electrode resistance $R_S$ into a corresponding output voltage $V_{Temp}$. It should be appreciated however that since the resistance variation of metals is usually small, an amplifier 90 may be used in the temperature sensor circuit 16c to properly detect the temperature. The output voltage ($V_{Temp}$) is then sent to the microcontroller 18 for further processing as described above.

Figure 4:
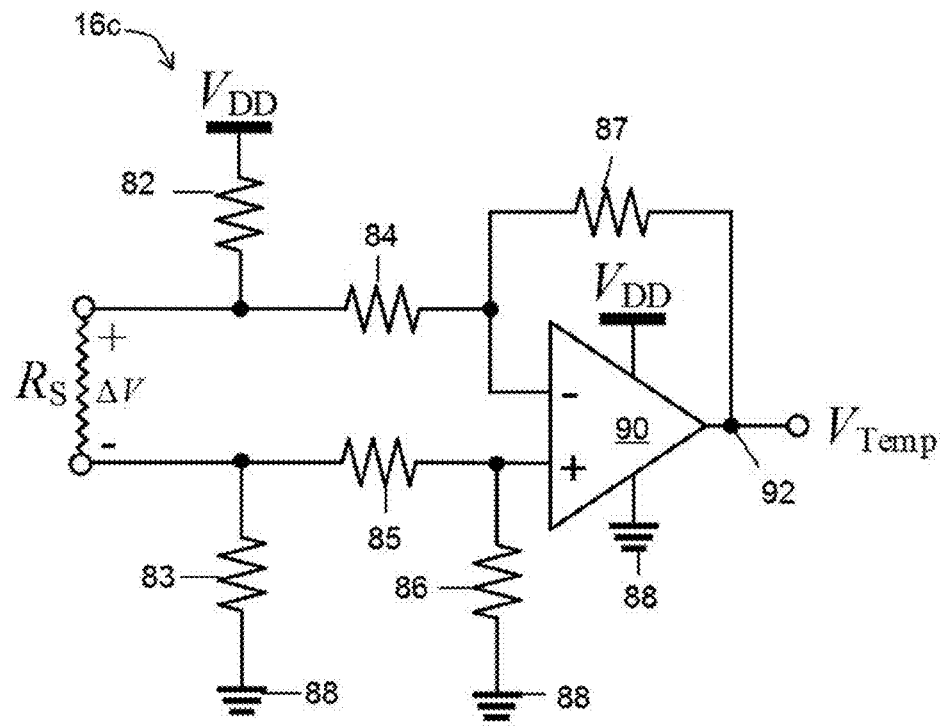
FIG. 4 is a schematic circuit diagram showing the operation of a temperature sensor for a water condition monitoring device according to at least one embodiment of the present invention.

In some embodiments, the temperature sensor circuit 16c may have the general layout shown in FIG. 4. It should be understood that with a given change in temperature of the water or other liquid being tested, the resistance of electrodes will vary based on their own temperature coefficients. In order to take advantage of the single-pair of electrodes 12, 14, the resistance of one of electrodes over a known length is measured to obtain the temperature of the water being tested. FIG. 4 shows a representative circuit that may be used to measure the resistance of electrode according to one or more embodiments of the present invention. In these embodiments, the temperature sensor may comprise a supply power source ($V_{DD}$), first resisters 82, 83 ($R_1$), second resisters 84, 85 ($R_2$), third resisters 86, 87 ($R_3$), grounds 88 and an operational amplifier 90 arranged as shown in FIG. 3, to produce an output voltage ($V_{Temp}$) at node 92. First resisters 82, 83 ($R_1$), second resisters 84, 85 ($R_2$), and third resisters 86, 87 ($R_3$) may be any suitable resister such as a fixed carbon resister, wire wand resister, metal film resistor, or the like. One or ordinary skill in the art will be able to select a suitable resistors for first resisters 82, 83 ($R_1$), second resisters 84, 85 ($R_2$), and third resisters 86, 87 ($R_3$) without undue experimentation.

In some embodiments, $V_{DD}$ may be a DC power source of from 3.3V to 5V depending upon the output range, but may be any appropriate value necessary to operate the operational amplifier 90. $R_S$ is the electrode resistance and may be expressed as:

$$R_S = \rho \frac{A}{l} \quad (4)$$

where ρ is electrical resistivity, A is the cross-sectional area and l is the length of electrode where the probes are connected. Resistance $R_S$ changes with temperature since ρ depends on temperature. The relationship between ρ and temperature may be given by the formula:

$$\rho(T)=\rho_0[1+\alpha(T-T_0)] \quad (5)$$

where α is temperature coefficient and $\rho_0$ is resistivity at $T_0$ for the metal. However, variation is defined by α (e.g. bigger α will make more resistance variations). However, since the temperature coefficient of metals is small, an operational amplifier 90 is required to detect the small voltage change due to temperature variation $\Delta V_{Temp}$, which is given by the formula:

$$\Delta V_{Temp} = -\frac{R_2}{R_1} \Delta V_S \quad (6)$$

where R<<$R_1$ and R<<$R_2$ are assumed. As a result, $\Delta V_{Temp}$ will be proportional to the temperature change of the solution.

In some embodiments, water condition monitoring device 10 may also include a dissolved oxygen sensor. In these embodiments, a voltage corresponding to the oxidation potential of oxygen is applied between the first and second metal electrodes 12, 14 and the current between the first metal electrode 12 or second metal electrode 14 and a third metal electrode (not shown) is measured. In this case, the amount or magnitude of residual current is proportional to the dissolved oxygen concentration level. An output voltage proportional to the dissolved oxygen concentration level is then sent to microcontroller 18, where it is converted to a dissolved oxygen value for later display or storage, as previously described.

The water condition monitoring device according to one or more embodiments of the present invention further includes microcontroller 18. Any suitable microcontroller may be used. While not intended to be limiting, suitable microcontrollers will preferably have at least: an analog to digital converter (ADC) with an input range of from about 0V to about 3.3V, 10 bit resolution, two or more timers, 8 KB of Random Access Memory (RAM), and 32 KB of flash memory, and should support serial and peripheral interfaces and devices. In some embodiments, microcontroller 18 may include integrated or remote memory and storage capacity. In some embodiments, suitable microcontrollers, may include without limitation, a PIC24 16-bit Microcontroller (part no. PIC24FJ32GA002) commercially available through Microchip Technologies (Chandler, Ariz.).

Microcontroller 18 will have one or more inputs for receiving sensor output. In some embodiments, microcontroller 18 will also include one or more input for receiving user input and programming. Microcontroller 18 will likewise have two or more inputs (not shown) for controlling sensors 16 and one or more outputs (not shown) for transmitting parameter values to a display, storage device, and/or network/wireless interface.

As set forth above, the operation of each sensor may be controlled by microcontroller 18, which, among other things, activates and deactivates operation of each one of the sensors 16. In the embodiment shown in FIG. 1, switches 94 ($S_1$), 96 ($S_2$) and 98 ($S_3$) are located between the electrodes 12, 14 and pH sensor circuit 16a, electrical conductivity sensor circuit 16b, and temperature sensor circuit 16c, respectively, and are coupled to microcontroller 18. Switches 94 ($S_1$), 96 ($S_2$) and 98 ($S_3$) are controlled by microcontroller 18 to enable the operation modes shown in Table 1.

TABLE 1

| Operation Mode | $S_1$ | $S_2$ | $S_3$ |
| --- | --- | --- | --- |
| pH sensing and output data generation | ON | OFF | OFF |
| EC sensing and output data generation | OFF | ON | OFF |
| Temp. sensing and output data generation | OFF | OFF | ON |

Because each of sensors 16 may utilize the first and second metal electrodes 12, 14 differently, it is contemplated that in most embodiments, only one of sensors 16a-c may be activated at a time. It should be appreciated, moreover, that the present invention is not to be limited to the switches shown in the embodiment of FIG. 1 and the microcontroller 18 may control the operation of each one of sensors 16 by any means known in the art for that purpose. In some embodiments, microcontroller 18 may control operation of each one of sensors 16 by controlling the power being delivered to each one of sensors 16 in turn.

In general operation, the microcontroller 18 activates sensors 16 one at a time, as set forth above. It processes the input it receives from one of sensors 16 activated, generating the appropriate parameter value for display or storage, before deactivating that sensor and activating the next one of sensors 16. It should be understood that each output voltage generated by sensors 16 corresponds to a particular parameter value. The present invention is not to be limited to a particular method of generating the appropriate parameter value based upon the sensor output.

In some embodiments, the analog output voltage signal received from sensors 16 is converted to a digital value by the microcontroller 18 and this digital value is then used to generate an appropriate parameter value. In some other embodiments, however, the analog output voltage may be converted to a digital value in sensors 16 (rather than microcontroller 18) and a digital signal containing data corresponding to sensors 16 output voltage is then sent from one of sensors 16 to microcontroller 18, where it is used to generate the appropriate parameter value.

Once the output voltages received from sensors 16 have been digitized, microcontroller 18 may use any method known in the art to generate an appropriate parameter value based upon that data. In some embodiments, these output voltages and corresponding parameter values are stored in microcontroller 18 in, for example, a reference table or look up table. In these embodiments, the data received from sensors 16 is compared to values in the appropriate look up table for that parameter to generate the appropriate parameter value. In some other embodiments, microcontroller 18 may calculate the appropriate parameter value based upon the data corresponding to the output voltage received from the sensor and other known variables. Once generated, each parameter value may then be stored, displayed or transmitted through a wireless communication unit to a remote location.

In one or more embodiments, the microcontroller 18 activates and deactivates each one of sensors (for example, sensors 16a-c) in turn in a continuous loop. By way of example, in one or more embodiments, the microcontroller 18 will activate a first sensor circuit 16a as set forth above and then process the inputs it received from that (first) sensor circuit 16a, generating the appropriate parameter value. Once generated, the parameter value may then be stored, displayed or transmitted through the wireless communication unit to a remote location. The microcontroller 18 then sends a signals deactivating the first sensor 16a and activating the next (second) sensor circuit 16b. The microcontroller then processes the input it receives from that (second) sensor circuit 16b, generating the appropriate parameter value, which may then be stored, displayed or transmitted through the wireless communication unit to a remote location. The microcontroller then sends a signals deactivating the second sensor circuit 16b and activating the next (third) sensor circuit 16c. It should be appreciated that water condition monitoring device 10 may contain more than three sensors circuits. The process is repeated until all of the sensors have been activated (and deactivated), at which time the first sensor circuit 16a is again activated and the cycle repeated. It should be appreciated, however, that so long as two sensors are not activated simultaneously, microcontroller 18 may be programmed to activate each of sensors 16 in any order, depending upon the particular application required.

Depending upon the application and the particular sensors involved, the microcontroller may generate a parameter value for each sensor many times per second. In some embodiments, the microcontroller may generate a parameter value for each sensor 10 times per second. In some embodiments, the microcontroller may generate a parameter value for each sensor two times per second. As a result, water condition monitoring device according to one or more embodiments of the present invention may provide measured values for multiple water parameters to a display in near real time.

Figure 5:
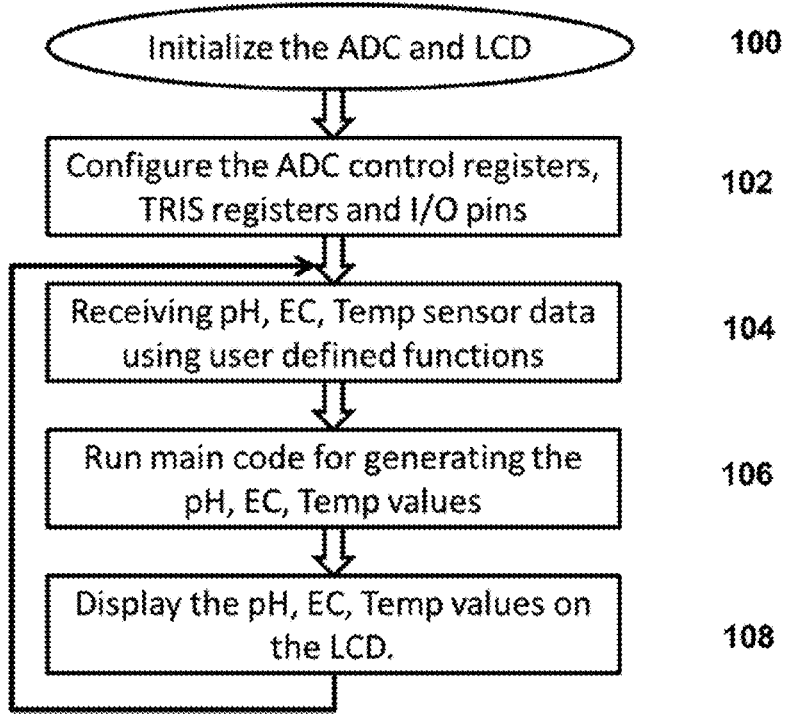
FIG. 5 is microcontroller program flowchart for a water condition monitoring device according to at least one embodiment of the present invention.

The programming necessary to instruct microcontroller 18 to perform the operating steps set forth above is well within the ability of one of ordinary skill in the art to do without undue experimentation. In some embodiments, the microcontroller 18 may be programmed to carry out an operation sequence that is consistent with the flow chart shown in FIG. 5. Initially, at step 100, the analog to digital converter (ADC) (not shown) and LCD display module (not shown) are initialized. In some embodiments, step 100 may also include initializing a comparator or other interface for transmission of sensor values to a remote location. Next, the ADC control registers, I/O pins, registers, and timers are configured 102.

The main programs consist of the user defined functions programmed into the microcontroller that receive and process the pH, EC, and temperature sensor data so that they can be displayed on the LCD. In step 104, the microcontroller receives and digitizes the analog signals received from the pH, EC, and temperature sensors using user defined (pre-programmed) functions. In some embodiments, the microcontroller may receive and digitize dissolved oxygen sensor signal received from the dissolved oxygen sensor using user defined (pre-programmed) functions. Next, in step 106, the microcontroller 18 runs the main code for generating the pH, EC, and temperature values for the pH, EC, and temperature sensor data received from the sensors.

In some embodiments, the main code also generates dissolved oxygen values from dissolved oxygen sensor data received from the dissolved oxygen sensor. In step 108, the microcontroller sends the pH, EC, and temperature values to the LCD display. In some embodiments, the microcontroller 18 sends the dissolved oxygen values to the LCD display. As the sensors are each activated, the microcontroller program periodically receives the newly generated sensor data and updates the pH, EC, and temperature values.

In light of the foregoing, it should be appreciated that the present invention significantly advances the art by providing a water condition monitoring device that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

A prototype of a water condition monitoring device according to one or more embodiments of the present invention was created with a 2 layer printed circuit board (PCB) that included a pH sensor circuit, an EC sensor circuit, a micro controller and the LCD display. A 9V battery was used as the main power source with two additional regulators that generated 3.3V and 5V from the 9V supply to power the sensor circuits, micro controller and LCD. In addition, an RAJ11 interface was implemented to enable on board microcontroller programming. A variable resistor was used for $R_4$ and $R_5$ of the EC circuit (See 38 ($R_4$) and 60 ($R_5$) on FIG. 3) to tune the oscillation frequency and adjust the amplitude of the AC voltage that was applied between the sensor electrodes. This can adjust the dynamic range and resolution of the EC circuit depending on the application conditions.

In order to measure the pH and EC using the sensor electrodes were placed in 300 ml of distilled water. For EC test, base was gradually added to the solution to make it ionized, and to increase the EC of the solution. The sensor output voltage and the EC value displayed on the LCD were observed. In general, hydroponics farmers and customers require EC meters that read from 0.5 to 3.0, thus our application was designed accordingly. For the pH test, the electrodes were placed in distilled water of 300 ml and for measurement were taken of the pH with low or high level of nutrients. Nutrient level of 0.4 ml and 0.6 ml were used for the low and high nutrient levels, respectively. After adding the nutrients to the distilled water, the solution was stirred and left idle for 30 minutes for the nutrients to settle down. After 30 minutes, the pH of the solution was adjusted to 5.5 (using a commercial pH meter). Then the pH was increased by gradually adding drops of base until it reached to 8. As the pH was changing, the output voltages of the sensor and pH value from the LCD display were recorded.

Example 2

In order to confirm that the output voltage of the proposed EC sensor corresponded to the actual EC value of a water sample, a commercial EC meter was used to map the sensor voltage to the EC value. The EC of the solution was changed from 0.1 siemens to 3.0 siemens, which is the general range for hydroponic applications, and the output voltage of the prototype EC sensor corresponding to the commercial EC meter readings were recorded. A relationship was found between the actual EC value and the proposed sensor output voltage. Based on the relationship between the sensor output voltage and the EC value, a curve fit equation is obtained. That is:

$$V_{EC} = m*EC + V_{EC0} \quad (7)$$

where m is the slope (m=0.3852), $V_{EC0}$ is the sensor output voltage for EC=0.1 (equal to 1.59V). This $V_{EC}$ is applied to the 10 bit ADC in the microcontroller, which generates digital output corresponding to the input voltage. Since the range of $V_{EC}$ is from 1.59 V to 2.75 V for EC=0.1 to 3.0, assuming a 10-bit ADC (output range 0~1023), the ADC will generate an output data between 496 and 853. Therefore, with ADC input range from 0 V to 3.3 V, the actual EC value from the ADC output is obtained using the below equation that is realized as the micro controller program:

$$EC = \frac{1}{m} * \left(\frac{3.3}{1024} * ADC\_EC\right) - \frac{1}{m} * \left(\frac{3.3}{1024} * ADC\_EC0\right) \quad (8)$$

where ADC_EC is the ADC output data for the EC and ADC_EC0 is the ADC output data for $V_{EC0}$. The above equation eight (8) shows the actual EC value processed from the micro controller, which is used for the LCD display.

Figure 6:
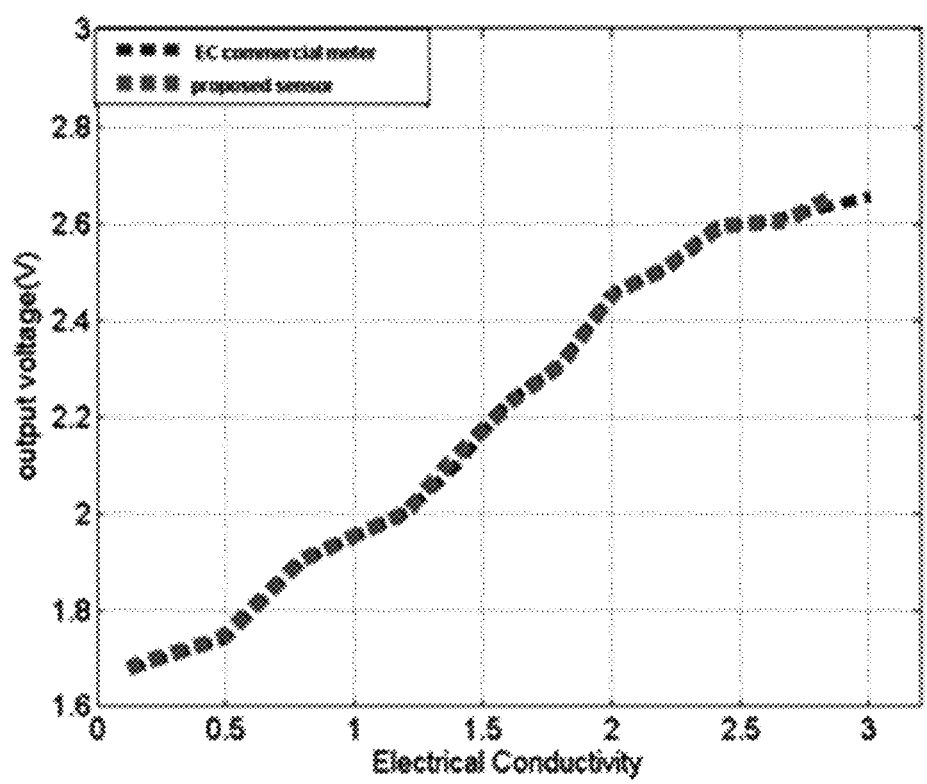
FIG. 6 is a graph showing results of electrical conductivity tests for a water condition monitoring device according to at least one embodiment of the present invention.

FIG. 6 shows the EC test results, where the dots shows the output voltage of the proposed sensor corresponding to each EC value and the dotted line is the reading from the commercial EC meter. The results show output voltage of the proposed sensor is linear with different EC values.

Example 3

Since the pH is also affected by the nutrient level, to determine the actual pH regardless of nutrient level two different programs were used to determine the pH value depending on the nutrient level (low or high). The nutrient level was determined by the EC, for an EC<1.5, low nutrient, and EC>1.5, high nutrient. In order to determine the output voltage of the proposed sensor corresponding to the actual pH value (first with low nutrient level), a commercial pH meter is used to map the sensor voltage to the actual pH value. The pH of the solution was changed from 5.5 to 8 which is the general range for the hydroponic applications, and the output voltage of the proposed sensor corresponding to the commercial pH meter readings were recorded. A relationship between the actual pH value and the proposed sensor output voltage was found. Based on the relationship between output voltage and pH, a curve fit equation for low nutrient level is obtained. That is:

$$V_{pHL} = m*pH - V_{pHL0} \quad (9)$$

where m is the slope (m=0.115) and $V_{pHL0}$ is the sensor output voltage for pH=0 (equal to 0.237V). This $V_{pHL}$ was applied to the 10 bit ADC, which generated a digital output corresponding to the input voltage. Since the range of $V_{pHL}$ is from 0.396V to 0.683 V for pH=5.5 to 8, the ADC will generate an output between 122 and 212. Assuming the input range of the ADC was from 0V to 3.3V, the actual pH value with low nutrient level, from the ADC output is obtained using the below equation.

$$pH\_L = \frac{1}{m} * \left(\frac{3.3}{1024} * ADC\_pHL\right) - \frac{1}{m} * \left(\frac{3.3}{1024} * ADC\_pHL0\right) \quad (10)$$

where ADC_pHL was the ADC output data for the pH and ADC_pHL0 was the ADC output data for $V_{pHL0}$. The above eq. (10) shows the actual pH value processed from the micro controller, which will be used for LCD display. The program for high nutrient level pH will be similar to the low nutrient level pH.

The only difference will be the curve fit equation, since in this case the sensor output voltage for the actual pH value will be different compared to the low nutrient level. That is:

$$V_{pHh} = m*pH - V_{pHh0} \quad (11)$$

where m is the slope (m=0.141) and $V_{pHL0}$ is the sensor output voltage for pH=0 (equal to 0.242V). For the high nutrient level, the sensor output voltage will be from 0.533V to 0.886V for pH=5.5 to 8. As a result, the ADC output will be between 165 and 274.

Figure 7A:
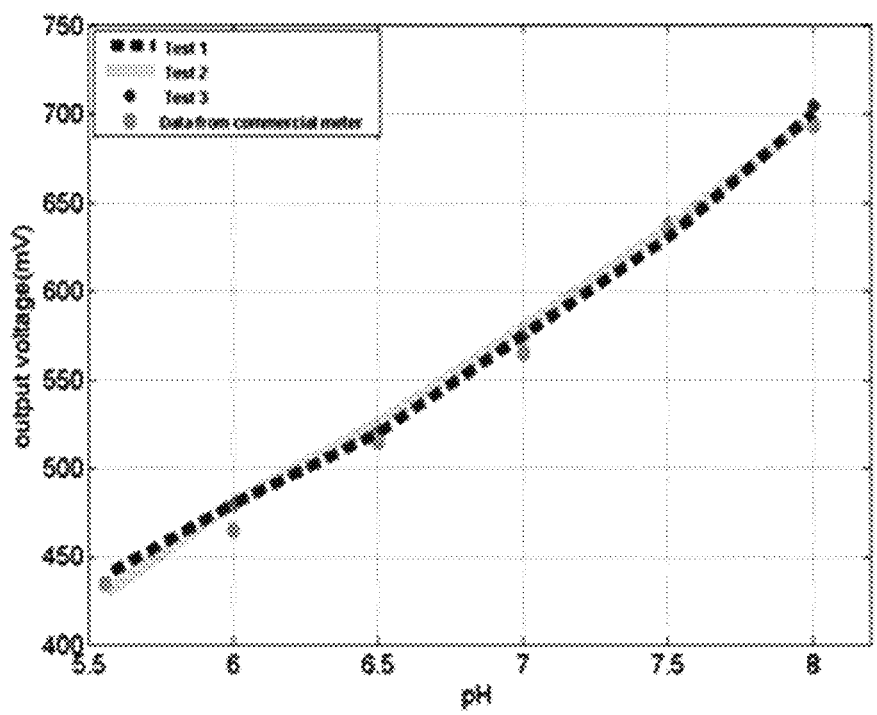
FIGS. 7A and 7B are graphs showing results of pH test results with (7A) low nutrient level. (7B) high nutrient level for a water condition monitoring device according to at least one embodiment of the present invention.
Figure 7B:
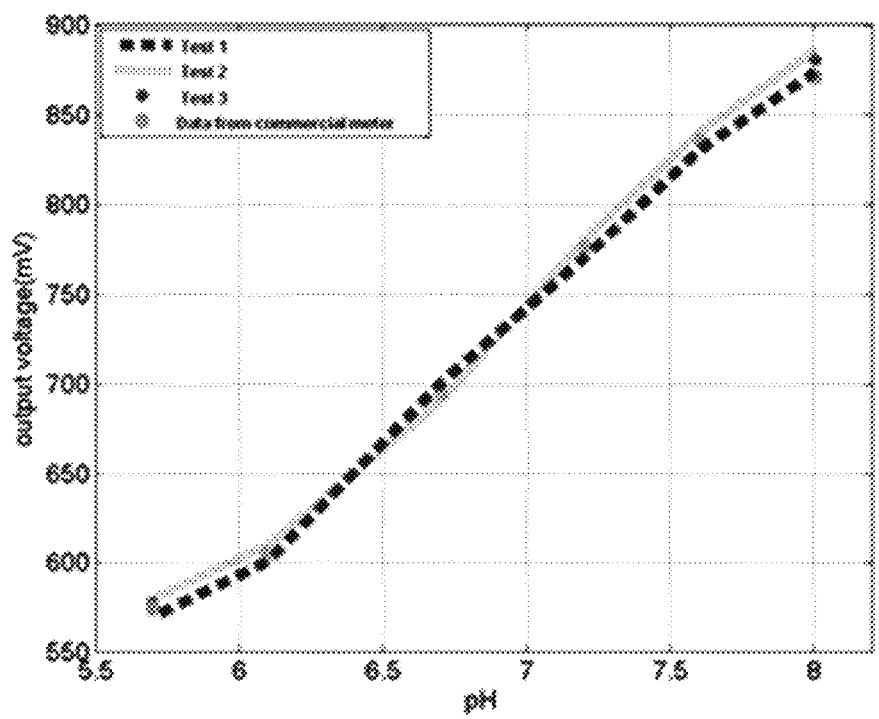

FIGS. 7A and 7B show the output voltage of one or more embodiments of the proposed sensor corresponding to pH value for low and high nutrient levels, respectively. Three identical tests 1, 2, 3 were performed to show the consistence of the results. For the pH test, the output voltage of the proposed sensor shows a linear relationship with the actual pH value for low and high nutrient levels. The sensor output voltages were higher for the high nutrient levels. Furthermore, the readings from the LCD display are consistent with the commercial pH meter values.

Example 4

Prophetic Example

It is believed that a microcontroller program for a temperature sensor circuit can be realized using a procedure similar to the procedures outlined above for the EC and pH sensor circuits.

What is claimed is:
1. A water condition monitoring device comprising:
a pair of metal electrodes comprising a first metal electrode and a second metal electrode, wherein said first and second metal electrodes are made from different conductive metals;
a pH sensing unit coupled to said pair of electrodes for sensing the pH of a sample; an electrical conductivity sensing unit coupled to said pair of electrodes for sensing the electrical conductivity of a sample; and
a microcontroller, coupled to said pH sensing unit and said electrical conductivity sensing unit.

2. The water condition monitoring device of claim 1, further comprising a temperature sensing unit coupled to said first or said second metal electrode for sensing temperature and said microcontroller.

3. The water condition monitoring device of claim 1, further comprising a dissolved oxygen sensing unit coupled to said pair of metal electrodes, a third electrode, and said microcontroller.

4. The water condition monitoring device of claim 2, further comprising a dissolved oxygen sensing unit coupled to said pair of metal electrodes, a third electrode, and said microcontroller.

5. The water condition monitoring device of claim 1 wherein said first metal electrode further comprises a metal selected from the group consisting of copper, zinc, nickel, platinum, silver, gold, and combinations thereof.

6. The water condition monitoring device of claim 1, wherein said second metal electrode further comprises a metal selected from the group consisting of copper, zinc, nickel, platinum, silver, gold, and combinations thereof.

7. The water condition monitoring device of claim 1, further comprising a display coupled to said microcontroller.

8. The water condition monitoring device of claim 1, further comprising an interface for storage or display of measured pH, electrical conductivity, temperature and/or dissolved oxygen values at a remote location.

9. A method of monitoring water conditions using a single set of metal electrodes comprising:
placing a pair of metal electrodes comprising a first metal electrode and a second metal electrode in a quantity of water to be monitored, wherein said pair of electrodes are coupled to a plurality of sensors, each sensor measuring an attribute of the water to be monitored using said pair of metal electrodes and said first metal electrode and said second metal electrode are made from different conductive metals; and
sequentially activating each one of said plurality of sensors to measure each attribute of the water to be monitored and generating a corresponding output voltage.

10. The method of monitoring water conditions of claim 9, wherein said plurality of sensors are coupled to a microcontroller, said method further comprising:
sending the output voltage produced by each one of the plurality of sensors to the microcontroller; and
comparing the output voltage of each sensor to a corresponding table of known attribute values to find an attribute value that corresponds to the output voltage.

11. The method of monitoring water conditions of claim 10, further comprising
storing or displaying the attribute value that corresponds to the output voltage of the sensor.

12. The method of monitoring water conditions of claim 1, wherein the plurality of sensors comprises a pH sensor for measuring the pH of the water using said pair of metal electrodes and an electrical conductivity sensor for measuring the electrical conductivity of the water using said pair of metal electrodes, said method further comprising:
sending a signal activating said pH sensor and causing it to measure the voltage difference between said first metal electrode and said second metal electrode of said pair of metal electrodes and generate a first output voltage corresponding to the pH of the water;
transmitting the first output voltage to a microcontroller;
converting the first output voltage to a corresponding pH value in said microcontroller;
storing or displaying said corresponding pH value;
sending a signal deactivating said pH sensor;
sending a signal activating said electrical conductivity sensor and causing it to apply an AC voltage across said first and second metal electrodes of said pair of metal electrodes, thereby generating a second output voltage that is proportional to the electrical conductivity of the water;
transmitting said second output voltage to said microcontroller;
converting said second output voltage to a corresponding electrical conductivity value in said microcontroller;
storing or displaying said electrical conductivity value; and
sending a signal deactivating said electrical conductivity sensing unit.

13. The method of monitoring water conditions of claim 9, wherein the plurality of sensors for measuring an attribute of the water to be monitored further comprise a temperature sensor for measuring the temperature of the water, said temperature sensor coupled to one of said first and second metal electrodes of said pair of metal electrodes, said method further comprising:
sending a signal activating said temperature sensor and causing it to apply a voltage to one of said first or said second metal electrodes of said pair of metal electrodes and to measure the resistance;
converting the resistance to a corresponding output voltage and sending said output voltage to the microcontroller;
converting said output voltage to a corresponding temperature value in said microcontroller;
storing or displaying said temperature value; and
sending a signal deactivating said temperature sensor.

14. The method of monitoring water conditions of claim 12, wherein the plurality of sensors for measuring an attribute of the water to be monitored further comprise a temperature sensor for measuring the temperature of the water, said temperature sensor coupled to one of said first and second metal electrodes of said pair of metal electrodes for measuring the temperature of the water, the method further comprising:
sending a signal activating said temperature sensing unit and causing it to apply a voltage to one of said first or said second metal electrodes of said pair of metal electrodes and to measure the resistance;
converting the resistance to a corresponding output voltage and sending said corresponding output voltage to the microcontroller;
converting said corresponding voltage to a temperature value in said microcontroller;
storing or displaying said temperature value; and
sending a signal deactivating said temperature sensing unit.

15. The method of monitoring water conditions of claim 9, wherein the plurality of sensors for measuring an attribute of the water to be monitored further comprise a dissolved oxygen sensing unit for measuring the level of dissolved oxygen in the water using said pair of metal electrodes, the method further comprising:
sending a signal activating said dissolved oxygen sensing unit and causing it to apply an oxidation potential voltage across said first and second metal electrodes of said pair of metal electrodes thereby causing the dissolved oxygen in the water to come out of solution;
measuring the voltage difference between the first metal electrode or the second metal electrode of said pair of metal electrodes and a third metal electrode and generating a corresponding output voltage;
transmitting said output voltage to the microcontroller;
converting said output voltage to a dissolved oxygen value in said microcontroller;
storing or displaying said dissolved oxygen value; and
sending a signal deactivating said dissolved oxygen sensing unit.

16. The method of monitoring water conditions of claim 12, wherein the plurality of sensors for measuring an attribute of the water to be monitored further comprise a dissolved oxygen sensing unit for measuring the level of dissolved oxygen in the water using said pair of metal electrodes, the method further comprising:
sending a signal activating said dissolved oxygen sensing unit and causing it to apply an oxidation potential voltage across said first and second metal electrodes of said pair of metal electrodes thereby causing the dissolved oxygen in the water to come out of solution;
measuring the voltage difference between the first metal electrode or the second metal electrode of said pair of metal electrodes and a third metal electrode and generating a corresponding output voltage;
transmitting said output voltage to the microcontroller;
converting said output voltage to a dissolved oxygen value in said microcontroller;
storing or displaying said dissolved oxygen value; and
sending a signal deactivating said dissolved oxygen sensing unit.

17. The method of monitoring water conditions of claim 14, wherein the plurality of sensors for measuring an attribute of the water to be monitored further comprise a dissolved oxygen sensing unit for measuring the level of dissolved oxygen in the water using said pair of metal electrodes, the method further comprising:
sending a signal activating said dissolved oxygen sensing unit and causing it to apply an oxidation potential voltage across said first and second metal electrodes of said pair of metal electrodes thereby causing the dissolved oxygen in the water to come out of solution;
measuring the voltage difference between the first metal electrode or the second metal electrode of said pair of metal electrodes and a third metal electrode and generating a corresponding output voltage;
transmitting said output voltage to the microcontroller;
converting said output voltage to a dissolved oxygen value in said microcontroller;
storing or displaying said dissolved oxygen value; and
sending a signal deactivating said dissolved oxygen sensing unit.

* * * * *